United States Patent [19]
Grubbs et al.

[11] Patent Number: 5,977,393
[45] Date of Patent: Nov. 2, 1999

[54] SCHIFF BASE DERIVATIVES OF RUTHENIUM AND OSMIUM OLEFIN METATHESIS CATALYSTS

[75] Inventors: Robert H. Grubbs, S. Pasadena, Calif.; Sukbok Chang, Seoul, Rep. of Korea; LeRoy Jones, II, Bolingbrook, Ill.; Chunming Wang, Highland Park, N.J.

[73] Assignee: California Institute of Technology, Pasadena, Calif.

[21] Appl. No.: 09/192,175

[22] Filed: Nov. 12, 1998

Related U.S. Application Data

[60] Provisional application No. 60/066,721, Nov. 21, 1997.

[51] Int. Cl.$^6$ ................................ C07F 15/00; C08F 4/80
[52] U.S. Cl. ............................ 556/21; 556/33; 556/137; 502/155; 502/162; 526/171; 526/172; 526/183; 526/190; 526/280; 526/281; 264/171.23; 264/171.28
[58] Field of Search ............................... 556/21, 33, 137; 502/155, 162; 526/171, 172, 183, 190, 280, 281, 283; 264/171.23, 171.28

[56] References Cited

U.S. PATENT DOCUMENTS

| | | | |
|---|---|---|---|
| 5,312,940 | 5/1994 | Grubbs et al. | 556/136 |
| 5,710,298 | 1/1998 | Grubbs et al. | 556/22 |
| 5,831,108 | 11/1998 | Grubbs et al. | 556/21 |

OTHER PUBLICATIONS

Chang, et al., Synthesis and Characterization of New Ruthenium–Based Olefin Metathesis Catalysts Coordinated with Bidentate Schiff–base Ligands. Organometallics, Aug. 3, 1998, vol. 17, No. 16, pp. 3460–3465.

El–Hendawy, Ahmed M., "Ruthenium(II) Complexes of O,N–Donor Schiff Base Ligands and Their Use as Catalytic Organic Oxidants", Polyhedron, vol. 12, No. 19, pp. 2343–2350 (1993).

Blaser, Hans–Ulrich, "The Chiral Pool as a Source of Enantioselective Catalysts and Auxillaries", Chem. Rev., vol. 92, pp. 935–952 (1992).

Nitta, Hideaki, et al., "Peptide–Titanium Complex as Catalyst for Asymmetric Addition of Hydrogen Cyanide to Aldehyde", J. Am. Chem. Soc., vol. 114, pp. 7969–7975 (1992).

Kureshy, Rukhsana I., et al., "Enantioselective catalytic epoxidation of nonfuctionalized prochiral olefins by dissymmetric chiral Schiff base complexes of Mn(III) and Ru(III) metal ions II", Journal of Molecular Catalysis A: Chemical 120, pp. 101–108 (1997).

Kureshy, R.I., et al., "Asymmetric Epoxidation of Styrene by Novel Chiral Ruthenium(II) Schiff Base Complexes, Synthesis and Characterization", Tetrahedron: Asymmetry, vol. 4, No. 7, pp. 1693–1701 (1993).

*Primary Examiner*—Porfirio Nazario-Gonzalez
*Attorney, Agent, or Firm*—Pillsbury Madison & Sutro LLP

[57] ABSTRACT

The present invention generally relates to ruthenium and osmium carbene catalysts for use in olefin metathesis reactions. More particularly, the present invention relates to Schiff base derivatives of ruthenium and osmium carbene catalysts and methods for making the same. The inventive catalysts are generally prepared by the treatment of unmodified catalysts with the salts of the desired Schiff base ligands, in which an anionic and a neutral electron donating ligands of the unmodified catalysts are simultaneously replaced. The Schiff base derivatives of the ruthenium and osmium carbene catalysts show unexpectedly improved thermal stability while maintaining high metathesis activity, even in polar protic solvents. Although the inventive catalysts may be used in all metathesis reactions, use of these catalysts for ring-closing metathesis ("RCM") reactions is particularly preferred.

25 Claims, No Drawings

SCHIFF BASE DERIVATIVES OF RUTHENIUM AND OSMIUM OLEFIN METATHESIS CATALYSTS

This application claims the benefit of U.S. Provisional Application No. 60/066,721, filed Nov. 21, 1997 by inventors Robert H. Grubbs, Sukbok Chang, Leroy Jones II, and Chunming Wang entitled "Schiff Base Derivatives of Ruthenium and Osmium Olefin Metathesis Catalysts." Provisional Patent Application No. 60/066,721 and accompanying Supplementary Materials filed therewith are incorporated herein by reference.

The United States Government has certain rights in this invention pursuant to Grant No. CHE 892272 awarded by the National Science Foundation.

BACKGROUND

A large number of catalyst systems that can initiate olefin have been introduced. However, most early work in olefin was done using ill-defined multi-component catalyst systems. It is only in recent years that well-defined single component metal carbene complexes have been prepared and extensively utilized in olefin metathesis.

With the advent of efficient catalyst systems, olefin metathesis has emerged as a powerful tool for the formation of C—C bonds in chemistry. Of importance among the well-defined catalyst systems is the alkoxy imido molybdenum system 1 developed by Schrock and co-workers and the benzylidene ruthenium carbene complexes 2-3 developed by Grubbs and co-workers.

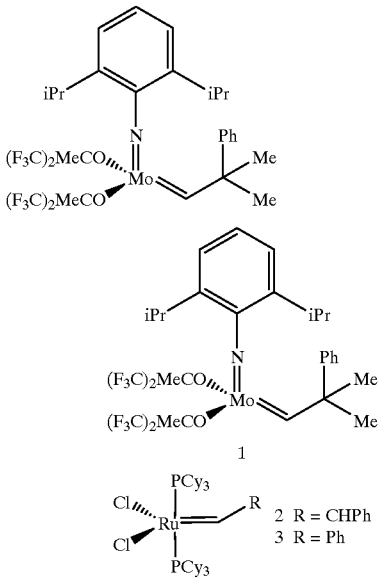

In particular, the ruthenium carbene catalyst systems have drawn a lot of attention, not only because they exhibit high reactivity for a variety of metathesis processes under mild conditions, but also because of their remarkable tolerance of many organic functional groups. However, although these ruthenium carbene catalysts (particularly complexes 2 and 3) have been used in diverse olefin metathesis reactions with remarkable success, further improvements such as better thermal stability, high activity in polar protic solvents, and chiral and cis/trans selectivity, are required to more fully exploit their commercial potential.

SUMMARY OF THE INVENTION

The present invention generally relates to ruthenium and osmium carbene catalysts for use in olefin metathesis reactions. More particularly, the present invention relates to Schiff base derivatives of ruthenium and osmium carbene catalysts and methods for making the same.

The Schiff base catalysts are of the general formula

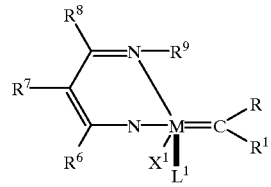

wherein:
M is ruthenium or osmium;
$X^1$ is an anionic ligand;
$L^1$ is a neutral electron donor;
R and $R^1$ are each hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, the substituent optionally substituted with one or more moieties selected from the group consisting $C_1$–$C_{10}$ alkyl, $C_1$–$C_{10}$ alkoxy, and aryl;
Z is selected from the group consisting of oxygen, sulfur,—$NR^{10}$, and —$PR^{10}$, and
$R^6$, $R^7$, $R^8$, $R^9$, and $R^{10}$ are each selected from the group consisting of hydrogen, $C_1$–$C_{20}$ alkyl, aryl, and heteroaryl, each non-hydrogen group optionally substituted with one or more moieties selected from the group consisting of $C_1$–$C_{10}$ alkyl, $C_1$–$C_{10}$ alkoxy, and aryl;
wherein $X^1$, $L^1$, Z, R, $R^1$, $R^6$, $R^7$, $R^8$, and $R^9$ each optionally includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

The Schiff base ligands are prepared by the condensation of comprising contacting a salt of a Schiff base having the formula

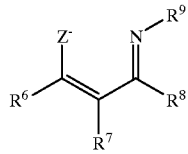

with compound having the formula

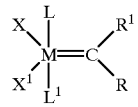

wherein
M, $X^1$, $L^1$, Z, R, $R^1$, $R^6$, $R^7$, $R^8$, and $R^9$ are as previously described;
X is an anionic ligand; and,
L is a neutral electron donor.

The Schiff base catalysts of the present invention show unexpectedly improved thermal stability over unmodified ruthenium and osmium catalysts, and maintain high metathesis activity even in polar protic solvents. Although the inventive catalysts may be used in all metathesis reactions, ring-closing metathesis ("RCM") reactions are particularly preferred since it is favored over other competing reactions at higher temperatures. In addition, because they provide convenient routes for including additional functionalities, Schiff base derivatives may play a key role in the design of chiral and/or cis/trans-selective metathesis catalysts.

DETAILED DESCRIPTION OF THE INVENTION

The present invention generally relates to ruthenium and osmium carbene catalysts for use in olefin metathesis reactions. More particularly, the present invention relates to Schiff base derivatives of ruthenium and osmium carbene catalysts and methods for making the same.

Unmodified ruthenium and osmium carbene complexes have been described in U.S. Pat. Nos. 5,312,940, 5,342,909, 5,728,917, 5,750,815, and 2 5 5,710,298, all of which are incorporated herein by reference. The ruthenium and osmium carbene complexes disclosed in these all possess metal centers that are formally in the +2 oxidation state, have an electron count of 16, and are penta-coordinated. These catalysts are of the general formula

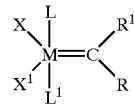

wherein:

M is ruthenium or osmium;

X and $X^1$ are each independently any anionic ligand;

L and $L^1$ are each independently any neutral electron donor ligand;

R and $R^1$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of these catalysts, the R substituent is hydrogen and the $R^1$ substituent is selected from the group consisting $C_1$–$C_{20}$ alkyl, $C_2$–$C_{20}$ alkenyl, and aryl. In even more preferred embodiments, the $R^1$ substituent is phenyl or vinyl, optionally substituted with one or more moieties selected from the group consisting of $C_1$–$C_5$ alkyl, $C_1$–$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl.

In preferred embodiments of these catalysts, L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L and $L^1$ are each a phosphine of the formula $PR^3R^4R^5$, where $R^3$, $R^4$, and $R^5$ are each independently aryl or $C_1$–$C_{10}$ alkyl, particularly primary alkyl, secondary alkyl or cycloalkyl. In the most preferred embodiments, L and $L^1$ ligands are each selected from the group consisting of -P(cyclohexyl)$_3$, -P(cyclopentyl)$_3$, -P(isopropyl)$_3$, and -P(phenyl)$_3$.

In preferred embodiments of these catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride.

The catalysts of the present invention are similar to the above catalysts except that X and L are simultaneously substituted with a Schiff base ligand of the general formula

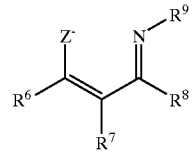

wherein:

N and Z are coordinated to the metal center, M;

Z is selected from the group consisting of O ("oxygen"), S ("sulfur"), $NR^{10}$, and $PR^{10}$; and $R^6$, $R^7$, $R^8$, $R^9$, and $R^{10}$ are each independently selected from a group consisting of hydrogen, $C_1$–$C_{20}$ alkyl, aryl, and heteroaryl. Each non-hydrogen group may be optionally substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl.

The term "alkyl" is intended to be inclusive and thus includes all forms of alkyl moieties such as include primarly, secondary, tertiary, and cyclo alkyl groups. Illustrative examples of aryl and heteroaryl moieties include but are not limited to: anthracyl, adamantyl, furyl, imidazolyl, isoquinolyl, phenyl, naphthyl, phenantracyl, pyridyl, pyrimidyl, pyrryl, and quinolyl. Moreover, adjacent R groups, $R^6$ and $R^7$, may together form a substituted or unsubstituted cyclic group (i.e. aryl, cycloalkyl, or heteroaryl). Each of $R^6$, $R^7$, $R^8$, $R^9$, and $R^{10}$ may be optionally substituted with one or more moieties selected from the group consisting of $C_1$–$C_{10}$ alkyl, $C_1$–$C_{10}$ and aryl. In addition, the Schiff base ligand may include one or more functional groups. Examples of suitable functional groups include but are not limited to: hydroxyl, thiol, thioether, ketone, aldehyde, ester, ether, amine, amide, nitro, carboxylic acid, disulfide, carbonate, isocyanate, carbodiimide, carboalkoxy, carbamate, and halogen.

The resulting catalysts are of the general formula

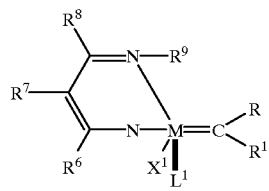

wherein M, R, $R^1$, $R^6$, $R^7$, $R^8$, $R^9$, Z, $X^1$, and $L^1$ are as previously defined.

In preferred embodiments: M is ruthenium; R is hydrogen; $R^1$ is selected from the group consisting of $C_1$–$C_{20}$ alkyl, $C_2$–$C_{20}$ alkenyl, and aryl; $L^1$ is a phosphine of the formula $PR^3R^4R^5$ wherein $R^3$, $R^4$, and $R^5$ are each selected from the group consisting of aryl, $C_1$–$C_{10}$ primary alkyl, secondary alkyl, and cycloalkyl; and, $X^1$ is selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and, trifluoromethanesulfonate.

In more preferred embodiments, the inventive catalysts are of the general formula

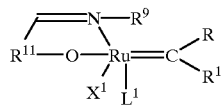

wherein R, $R^1$, $R^9$, $X^1$, and $L^1$ are as previously defined, and $R^{11}$ is an aryl or heteroaryl group, optionally substituted with one or more moieties selected from the group consisting of $C_1$–$C_{10}$ alkyl, $C_1$–$C_{10}$ alkoxy, and aryl. With reference to the general formula for the Schiff base catalyst derivative, M is ruthenium; Z is oxygen; $R^8$ is hydrogen, and $R^{11}$ is an aryl or heteroaryl group that is formed by the joining of $R^6$ and $R^7$.

In even more preferred embodiments of the Schiff base complexes:

$X^1$ is chloride;

$L^1$ is selected from the group consisting of -P(cyclohexyl)$_3$, -P(cyclopentyl)$_3$, -P(isopropyl)$_3$, and -P(phenyl)$_3$;

R is hydrogen;

$R^1$ is phenyl or vinyl, optionally substituted with one or more moieties selected from the group consisting of $C_1$–$C_5$ alkyl, $C_1$–$C_5$ alkoxy, and phenyl;

$R^9$ is an aryl or heteroaryl substituted with at least one moiety off its aromatic ring; and $R^{11}$ is an aryl or heteroaryl substituted with at least one electron withdrawing group. In especially preferred embodiments, $R^9$ is phenyl substituted with at least one bulky substituent and at least one electron withdrawing group, and $R^{11}$ is phenyl substituted with at least one electron withdrawing group. Suitable examples of electron withdrawing groups include but are not limited to: halide, $C_1$–$C_{10}$ alkyl substituted with one or more halides, and nitro. Suitable examples of bulky substituents include but are not limited to tertiary $C_3$–$C_{10}$ alkyl and aryl.

Two of the most preferred embodiments of the present invention include:

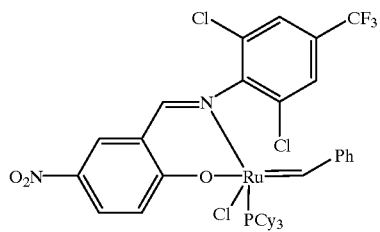

and

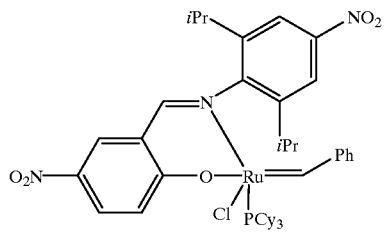

In addition to being valuable in their own right, the chelate structure of the inventive Schiff base compounds provide a sufficiently rigid structure for the design of chiral and/or cis/trans-selective metathesis catalysts. For example, depending on the nature of the reaction, it may be desirable to have the catalyst be chiral or prochiral. Illustrative uses of such compounds include the kinetic resolution of chiral olefins and assymetric induction in prochiral triene ring closing reactions. Cis/trans-selectivity may be achieved by controlling the steric bulk of the ligands to influence the relative energies of the reaction intermediates that lead to different products.

In another embodiment of the present invention, methods for preparing the Schiff base complexes are presented. In general the method reacting a salt of a Schiff base of the general formula

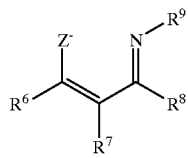

with a catalyst of the general formula

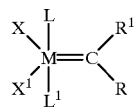

wherein M, R, $R^1$, $R^6$, $R^7$, $R^8$, $R^9$, X, $X^1$, L and $L^1$ are as previously defined.

Although any salt may be formed, thallium salts were found to be particularly effective.

In preferred embodiments, the Schiff base is formed from the condensation of an aldehyde or a ketone of the general formula

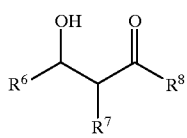

with an amine of the general formula $H_2NR^9$.

In more preferred embodiments, the condensation reaction is between an aldehyde, $R^{11}(HC=O)(OH)$, and an amine, $H_2NR^9$, to yield catalysts of the general formula

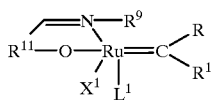

wherein $X^1$, $L^1$, $R$, $R^1$, $R^9$, and $R^{11}$ are as previously described. Particularly preferred aldehydes include substituted and unsubstituted salicylaldehyde.

For the purposes of clarity, the synthesis of the Schiff base derivatives of ruthenium and osmium catalysts will be illustrated with reference to specific catalyst embodiments, ruthenium complex 2 or 3. However, it should be understood that the forthcoming methods are generally applicable.

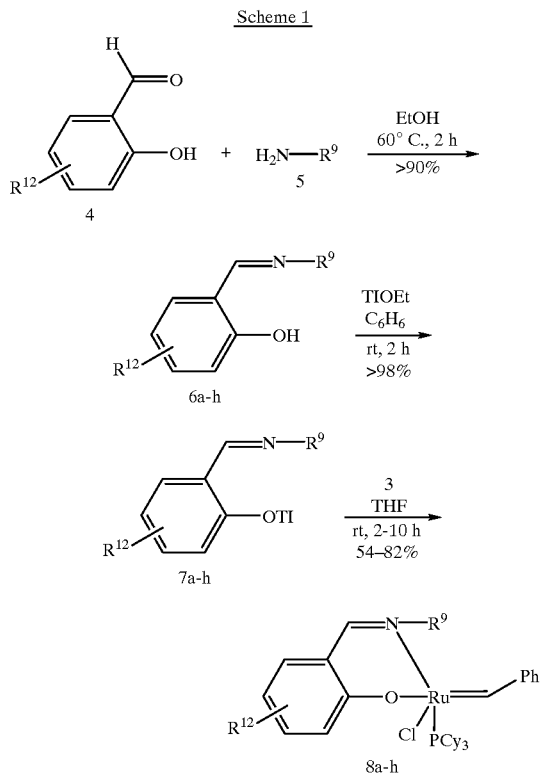

-continued a $R^{12} = H$, $R^9 = 2, 6\text{-i-PrC}_6H_3$
b $R^{12} = 4\text{-NO}_2$, $R^9 = 2, 6\text{-i-PrC}_6H_3$
c $R^{12} = 4\text{-NO}_2$, $R^9 = 2, 6\text{-Me-4-MeOC}_6H_2$
d $R^{12} = 4\text{-NO}_2$, $R^9 = 2, 6\text{-Me-4-BrC}_6H_2$
e $R^{12} = 4\text{-NO}_2$, $R^9 = 2, 6\text{-Cl-4-CF}_3C_6H_2$
f $R^{12} = 6\text{-Me-4-NO}_2$, $R^9 = 2, 6\text{-i-PrC}_6H_3$
g $R^{12} = 4\text{-NO}_2$, $R^9 = 2, 6\text{-i-Pr-4-NO}_2\text{-C}_6H_3$
h $R^{12} = 4\text{-NO}_2$, $R^9 = $

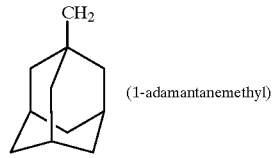

(1-adamantanemethyl)

As illustrated by Scheme 1, salicylaldimine ligands 6a–h were prepared by simple condensation of salicylaldehydes 4 and aliphatic or aromatic amine derivatives 5 in excellent yields. The salicylaldimine ligands were 5 quantitatively converted to the corresponding thallium salts upon treatment with thallium ethoxide. The resulting Schiff base ligands were substituted for X and L ligands in complex 2 or 3.

The efficiency of the substitution reactions to yield the desired Schiff base catalysts 8a–h varied depending on the bulk of the substituents on the ligands. For example, while thallium salts of ligands bearing a methyl group (7f) on the 6-position of the phenoxy part readily underwent substitution with 2 or 3, the reaction of ligands bearing bulkier substituents (i.e., t-Bu group) on the same position gave poor conversion under various substitution conditions. Reaction of 3 with ligands derived from anilines having number 2-and 6-substituents produced multiple complexes. However, presumably due to the steric reasons, ligands bearing highly bulky groups (i.e., triisopropylsilyloxy-) on the 2-and 6-position of benzimine exhibited relatively very poor reactivity in the reaction with 3. Nevertheless, the Schiff base ligand substitution described above is surprisingly robust and allows for the synthesis of a diverse set of Schiff base catalysts.

Despite the quantitative conversion (by NMR) of 3 to the Schiff base ruthenium complexes in all cases, isolated recrystallization yields were lower due to the high solubility of the product complexes in most organic solvents. The ruthenium Schiff base benzylidene species 8a–h are very stable solids to air or moisture, and in some cases, can be further purified by column chromatography using silica gel. Moreover, the complexes show negligible amounts of decomposition in solution ($CH_2Cl_2$ or $C_6H_6$), even when heated at temperatures as high as 85° C. For example, as shown by Table 1, although ruthenium complex 3 (a representative example of a previously described ruthenium metathesis catalysts) decomposed significantly after only 30 minutes at 85° C., inventive complex 8b was virtually unaffected.

TABLE 1

Comparisons of Catalyst Decomposition Rates

|  | complex 3 | complex 8b |
|---|---|---|
| Initial concentration | 4.2 mmoles | 4.0 mmoles |
| 30 minutes at 85° | 1.3 mmoles | 3.6 mmoles |
| 60 minutes at 85° | 0.6 mmoles | 3.8 mmoles |

As it will be explained in greater detail below, the unexpected increase in thermal stability of these catalysts over the previously described ruthenium and osmium metathesis catalysts makes them much more amenable to industrial applications.

Structural Characterization of the Schiff Base Substituted Ruthenium Complexes.

Substitution of one phosphine and one chloride ligand with a Schiff base ligand was unambiguously indicated by characteristic NMR spectral changes for all substitution reactions (7→8, Scheme 1). The coupling constants between the carbene proton Hα and the coordinated phosphine has been found to be sensitive to the relative orientation of the plane defined by the atoms of the carbene fragment and that of the P-Ru-P plane. When the carbene plane is 90° to the P-Ru-P plane, $J_{PH}$=0 and $J_{PH}$>10 when they are coplanar.

In contrast to complex 3 (singlet, 20.1 ppm in $CD_2Cl_2$), the chemical shifts of the benzylidene proton in the compounds 8a–h appear between 19.8 and 18.7 ppm as doublet (Table 2). As expected, the complexes bearing ligands with more electron withdrawing substituents were shifted to more downfield. Proton-phosphorous couplings also varied depending on the nature of the Schiff base ligands. Especially noteworthy is that coupling constants $J_{PH}$ are more sensitive to the steric bulk rather than electronic contribution of the substituents on the Schiff base ligands. This suggest that although the ligand coordination around the ruthenium metal center is similar, the relative geometry of each species varies slightly depending on the steric demands caused by the ligands. For instance, while sterically crowded ligands give lower JPH coupling constants (i.e., 2.7 Hz in 8f), those values increase upon reduction of steric demands in the Schiff bases (i.e., 4.8 Hz in 8d). As found in the proton NMR spectroscopy, the $^{31}P$ spectra for the coordinated phosphine ligands in 8a–h are also dependent on the electronic nature of the Schiff base ligands. For instance, while chemical shift of phosphorus is in the range of 51–54 ppm for aniline derived ligands, it is shifted to upfield (39 ppm) for 8h.

TABLE 2

NMR Data for Ruthium Carbene Complexes
8a–8h and J (in Hz, $CD_2Cl_2$)

| entry | compound | $^1H\alpha$ | $J_{HP}$ | $^{31}P$ |
|---|---|---|---|---|
| 1 | 8a | 19.68 | 3.6 | 52.23 |
| 2 | 8b | 19.77 | 3.3 | 52.23 |
| 3 | 8c | 19.49 | 4.7 | 50.51 |
| 4 | 8d | 19.48 | 4.8 | 50.62 |
| 5 | 8e | 19.39 | 4.5 | 50.65 |
| 6 | 8f | 19.69 | 2.7 | 53.50 |
| 7 | 8g | 19.72 | 3.3 | 52.54 |
| 8 | 8h | 18.68 | 13.5 | 38.95 |

Representative of complexes 8a–h, the structure of the Schiff base substituted benzylidene species 8b was further confirmed by a single crystal X-ray analysis. The crystal suitable for X-ray structure determrnination were isolated from concentrated diisopropyl ether solution at −20° C. The data collection and refinement data of the analysis is summarized in Table 3 and selected bond distances and angles are listed in Table 4.

TABLE 3

Summary of Crystal Data and Structure Refinements of 8b

| | |
|---|---|
| Empirical formula | $C_{44}H_{60}ClN_2O_3PRu \cdot 0.31\ CH_2Cl_2 \cdot 0.17\ H_2O$ |
| Formula weight | 863.53 |
| Crystal system | Prismatic Monoclinic (dark brown) |
| Space group | $P2_1/c$ (#14) |
| Temperature | 160K |

TABLE 3-continued

Summary of Crystal Data and Structure Refinements of 8b

| | |
|---|---|
| Unit cell dimensions | a = 9.123 (4) Å |
| | b = 24.320 (7) Å |
| | c = 19.863 (5) Å |
| Z | 4 |
| Volume | 4405 (3) Å$_3$ |
| μ | 5.30 cm$^{-1}$ ($\mu r_{max}$ = 0.13) |
| 2Θ | 3–5° |
| Crystal size (mm) | 0.10 × 0.13 × 0.44 |
| Reflections measured | 17106 |
| Independent reflections | 7741 |
| Goodness-of-fit on $F^2$ | 1.64 for 658 parameters and 7741 reflections |
| Final R indices [$F_o$] | 0.079 for 5735 reflections with $F_o^2 > 2\sigma(F_o^2)$ |
| Final weighted R [$F_o^2$] | 0.121 for 7741 reflections |

TABLE 4

Selected Bond Lengths (Å) and Angles (deg)
for Ruthenium Complex 8b

Bond Lengths (Å)

| | | | |
|---|---|---|---|
| Ru—Cl | 1.85 (6) | P—C33 | 1.860 (6) |
| Ru—O1 | 2.055 (4) | P—C39 | 1.862 (6) |
| Ru—N1 | 2.106 (4) | O1-C20 | 1.288 96) |
| Ru—P | 2.345 (2) | N1-C8 | 1.473 (7) |
| Ru—C1 | 2.382 (2) | N1-C14 | 1.301 (7) |
| C1-C2 | 1.451 (8) | C14-C15 | 1.433 (8) |
| P—C27 | 1.864 (7) | C1-H1 (Carbene H) | 0.94 (6) |

Bond Angles (degree)

| | | | |
|---|---|---|---|
| C1-Ru—O1 | 98.1 (2) | C8-N1-Ru | 121.5 (3) |
| C1-Ru—N1 | 103.5 (2) | C33-P—Ru | 114.2 (2) |
| O1-Ru—N1 | 88.9 (2) | C39-P—Ru | 117.5 (2) |
| C1-Ru—P | 96.8 (2) | C27-P—Ru | 102.4 (2) |
| O1-Ru—P | 88.4 (1) | C33-P—C39 | 11.7 (3) |
| N1-Ru—P | 159.8 (1) | C33-P—C27 | 103.9 (3) |
| C1-Ru—Cl | 88.7 (2) | C33-P—C27 | 105.2 (3) |
| O1-Ru—Cl | 173.0 (1) | O1-C20-C15 | 124.7 (5) |
| P—Ru—Cl | 89.0 (1) | N1-C14-C15 | 129.4 (5) |
| Ru—C1-H1 | 113.1 (36) | C2-C1-H1 | 111.6 (36) |

In the solid state, the molecule adopts a distorted trigonal bipyramidal coordination geometry. The bulky 2,6-diisopropyl benzimine occupies an axial position trans to the tricyclohexyl phosphine and the phenoxy part is positioned at an equatorial position with a nearly linear O1-Ru-Cl angle (173.0°). The two aromatic rings of the Schiff base ligand are positioned with respect to each other at a 80.1° angle. While the benzylidene moiety in complex 3 is perpendicular to the P1-Ru-P2 plane, the angle of the carbene unit in the structure of 8b to the P-Ru-N1 plane is 87.14°. This distortion of the carbene plane is consistent with the nonzero value of $J_{PH}$ for 8b. The Ru-Cl (carbene carbon) bond distance [1.850(6)Å] are similar to those in related compounds; $RuCl_2(=CHCH=CPh_2)PCy_3$ [d(Ru-C), 1.851(21) Å], $[RuCl(=C(OMe)-(CH=CPh_2)(CO)(Pi-Pr_3)_2][BF_4]$ [d (Ru-C), 1.874(3)Å] or $RuCl_2(=CH-p-C_6H_4Cl)(PCy_3)_2$ [d(Ru-C), 1.838(3)Å].

Use of the Schiff Base Derivatives in Metathesis Reactions

The inventive Schiff base catalysts may be used for any metathesis reaction. In general, methods for performing metathesis reactions comprise contacting at least one of the inventive catalyst with an olefin. Practice of the present invention may occur either in the presence or absence of solvents. In solventless reactions, the inventive catalysts typically dissolve in the olefin being reacted. As used herein, the term "olefin" is an unsubstituted or substituted hydrocarbon with at least one carbon-carbon double bond. The hydrocarbon may be straight-chain, branched, or a cyclic compound. Illustrative examples of hydrocarbon substituents include but are not limited to: $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl, $C_1$–$C_{20}$ alkylsulfinyl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

One particularly important metathesis reactions is ring opening metathesis polymerization ("ROMP") of cyclic olefins. Illustrative examples of cyclic olefins for ROMP include but are not limited to norborene, cyclobutene, norbornadiene, cyclopentene, dicyclopentadiene, cycloheptene, cyclooctene, 7-oxanorbornene, 7-oxanorbornadiene, cyclooctadiene, and cyclododecene. Another important metathesis reaction is is ring closing metathesis ("RCM). In RCM, a non-cyclic diene (an olefin having two carbon-carbon double bonds) is contacted with at least one of the inventive catalysts to form a cyclic olefin. Although the inventive catalysts may be used in any metathesis reaction, the use in RCM reactions is particularly preferred because it is favored over competing reactions at higher temperatures.

Scheme 2 illustrates the use of the Schiff base ruthenium carbene complexes 8a–h in an RCM reaction.

Scheme 2

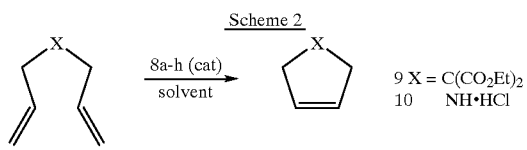

9 X = C(CO$_2$Et)$_2$
10    NH•HCl

In general, the inventive compounds tend to be less reactive at room 10 temperature than the previously described ruthenium and osmium carbene complexes. However, the reactivity increases dramatically at higher temperature. For instance, although the ring closure of diethyl diallylmalonate ester 9 proceeds in 12 hour at room temperature with complex 8g (8 mol %, $CH_2C_2$), the reaction is completed in 1 hour at 70° C. with the same carbene catalyst (3 mol %, $C_6H_6$). In another example, the use of complex 8b results in nearly 100% yield when the reaction is carried at 55° C. with no evidence of catalyst decomposition even after 2 days at that temperature. This high product yield is a surprising and unexpected result because of the number of competing pathways for diene reactants.

The pronounced difference in reactivities between room and elevated temperatures poses several advantages to the industrial use of these catalysts. For example, the use of the Schiff base catalysts of the present invention presents an elegant and simple method for controlling the pot life (which is the time during which the monomer/catalyst mixture may be worked on) of the polymerization reaction mixture. Relying on the temperature dependent kinetics of the polymerization reaction, all the pre-polymerization steps for making a molded part (i.e mixing the olefin monomer with catalyst, casting/injecting/pouring the reaction mixture into a mold) can occur at room temperature. Since the inventive catalysts are not very active at this temperature, the preparatory steps can occur without fear of premature polymerization. Once the reaction is ready to proceed, the mixture can be heated to the necessary temperature to allow the polymerization reaction to occur at the desired rate. Suitable temperatures will depend on the specific inventive catalyst. However, the elevated temperature is typically at least about 40° C.

In another example, the catalysts of the present invention may be used for the formation large molded products. The polymerization of thick parts has been particularly problematic because the exothermic nature of the reaction tended to kill the previously described metathesis catalysts during the course of the polymerization reaction. As a result, polymerization of these products tended to be uneven with the centers of thick regions being especially susceptible to incomplete polymerization. In contrast, because of their increased thermal stability, such problems may be avoided with the use of the inventive catalyst.

Yet another feature of the catalysts of the present invention is their ability to retain catalytic activity even in polar protic solvents. The use of polar protic solvents is necessary particularly when a desired substrate is not soluble in common nonpolar solvents. For example, diallylamine HCl salt 10 which is not soluble in common nonpolar solvents was cleanly cyclized in methyl alcohol with complex 8a (5 mol %, 40° C., 12 h).

In summary, the Schiff base derivatives of ruthenium and osmium complexes are important catalysts in their own right exhibiting high thermal stability and high metathesis activity (even in polar protic solvents). In addition, because they provide convenient routes for including additional functionalities, Schiff base derivatives may play a key role in the design of chiral or cis/trans-selective olefin metathesis catalysts.

Experimental Section

Unless otherwise noted, all operations were carried out using standard Schlenk techniques or dry-box procedures. Argon was purified by passage through columns of BASF R3-11 catalyst (Chemalog) and 4 Å molecular sieves (Linde). Solid organometallic compounds were transferred and stored in a nitrogen-filled Vacuum Atmospheres drybox. $^1$H-NMR (300.1 MHz) and $^{13}$C-NMR (75.49 MHz) spectra were recorded on a General Electric QE-300 spectrometer. $^{31}$P-NMR (161.9 MHz) spectra were recorded on a JEOL GX-400 spectrometer. NMR Chemical shifts are reported in ppm downfield from tetramethylsulane ("TMS") (δ scale) with TMS employed as the internal solvent for proton spectra and phosphoric acid employed as the internal solvent for phosphorous spectra. High-resolution mass spectra were provided by the Southern California Mass Spectrometry Facility (University of California, Riverside). Analytical thin-layer chromatography ("TLC") was performed using silica gel 60 F254 precoated plates (0.25 mm thickness) with a fluorescent indicator. Flash column chromatography was performed using silica gel 60 (230–400 mesh) from EM Science. All solvents were rigorously degassed in 18 L reservoirs and passed through two sequential purification columns. Complex 3 and 2,6-dimethyl-4-methoxyaniline were prepared according to published procedures (Nguyen et al., *J Am. Chem. Soc.* 115: 9858–9859 (1993); Sone et al., *Nippon Kagaku Kaishi* 7 1237–1240 (1982)). Unless otherwise noted, all other compounds were purchased from Aldrich Chemical Company and used as received.

General Procedure for Preparation of Schiff Base (6a–h).

The condensation of salicylaldehydes with aliphatic or aromatic amine derivatives were carried out with stirring in ethyl alcohol at 80° C. for 2 hours.

Upon cooling to 0° C., a yellow solid precipitated from the reaction mixture.

The solid was filtered, washed with cold ethyl alcohol and then dried in vacuo to afford the desired salicyladimine ligand in excellent yields. Any modifications are described for each reaction.

Schiff Base 6a ($R^1$=H, $R^2$=2,6-i-Pr$C_6H_3$):

Salicylaldehyde (0.37 g, 3.0 mmol), 2,6-diisopropylaniline (0.53 g, 3.0 mmol) and ethanol (15 mL) afforded 0.76 g (90%) of the title compound as a yellow solid. A drop of formic acid was used to accelerate the condensation reaction. mp. 60–61° C.; $^1$H-NMR (CDCl$_3$) δ 13.16 (s, 1H), 8.34 (s, 1H), 7.46 (d, J=7.2 Hz, 1H), 7.40 (t, J=7.2 Hz, 1H), 7.22 (bs, 3H), 7.10 (d, j=8.4 Hz, 1H), 6.99 (t, J=7.5 Hz, 1H), 3.20 (septet, J=6.6 Hz, 2H), 1.20 (d, J=6.9 Hz, 12H); $^{13}$C-NMR (CDCl$_3$)δ 166.4, 161.0, 145.9, 138.4, 133.0, 132.0, 125.3,123.0, 118.8, 118.4, 117.1, 27.9, 23.3; HRMS (EI) for $C_{19}H_{23}NO$ [M]$^+$281.1780, found 281.1786.

Schiff Base 6b ($R^1$=4-NO$_2$, $R^2$=2,6-i-Pr$C_6H_3$):

5-Nitrosalicylaldehyde (1.10 g, 6.60 mmol), 2,6-diisopropylaniline (1.20 g, 6.60 mmol) and ethanol (25 mL) afforded 2.0 g (93%) of the title compound as a yellow solid. mp. 122–124° C.; $^1$H-NMR (CDCl$_3$) δ 14.35 (s, 1H), 8.43 (s, 1H), 8.38 (d, J=2.7 Hz, 1H), 8.32 (d, J=9.3 Hz, 1H), 7.25 (bs, 3H), 7.15 (d, J=9.0 Hz, 1H), 2.97 (septet, J=6.9 Hz, 2H), 1.22 (d, J=6.9 Hz, 12H); $^{13}$C-NMR (CDCl$_3$) δ 166.8, 165.2, 144.4, 139.7, 138.4, 128.3, 128.2, 126.1, 123.3, 118.3, 117.3, 28.1, 23.3; HRMS (CI) for $C_{19}H_{23}N_2O_3$[M+H]$^+$ 327.1709; found 327.1708.

Schiff Base 6c ($R^1$=4-NO$_2$, $R^2$=2,6-Me-4-MeO$C_6H_2$):

5-nitrosalicylaldehyde (6.68 g, 40 mmol), 2,6-dimethyl-4-methoxyaniline (6.65 g, 44 mmol) and ethanol (140 mL) afforded 11.52 g (96%) of the title compound as a yellow solid. mp. 122–124° C.; $^1$H-NMR (CDCl$_3$) δ 14.67 (s, 1H), 8.41 (s, 1H), 8.33 (d, J=2.7 Hz, 1H), 8.28 (dd, J=9.1, 2.7 Hz, 1H), 7.10 (d, J=9.1 Hz, 1H), 6.68 (s, 2H), 3.81 (s, 3H), 2.24 '(s, 6H); $^{13}$C-NMR (CDCl$_3$) δ 167.6, 165.0, 157.3, 130.2, 128.3, 128.2, 118.5, 117.5, 113.9, 55.4, 18.9; HRMS (CI) for $C_{16}H_{17}N_2O_4$ [M+ $^H$]$^+$301.1188, found 301.1196. found 301.1196.

Schiff Base 6d ($R^1$=4-NO$_2$, $R_2$=2,6-Me-4-Br$C_6H_2$):

5-Nitrosalicylaldehyde (0.67 g, 4.0 mmol), 4-bromo-2,6-dimethylaniline (0.80 g, 4.0 mmol) and ethanol (15 mL) afforded 1.41 g (91%) of the title compound as a yellow solid. mp. 194–196° C.; $^1$H-NMR (CDCl$_3$) δ 13.96 (s, 1H), 8.41 (s, 1H), 8.35 (d, J=2.7 Hz, 1H), 8.30 (d, J=9.0 Hz, 1H), 7.28 (s, 2H), 7.13 (d, J=9.0 Hz, 1H), 2.19 (s, 6H); $^{13}$C-NMR (CDCl$_3$) δ 166.4, 165.5, 145.6, 139.8, 131.0, 130.2, 128.4, 128.2, 118.5, 118.2, 117.3, 18.1; MS (CI) 350 (100), 348 (92), 268 (29), 131 (91), 104 (25), 77 (29).

Schiff Base 6e ($R^1$=4-NO$_2$, $R^2$=2,6-Cl-4-CF$_3C_6H_2$):

5-Nitrosalicylaldehyde (1.30 g, 8.0 mmol), 4-animo-3,5-dichlorobenzotrifluoride (1.80 g, 8.0 mmol) and ethanol (25 mL) afforded 2.70 g (90%) of the title compound as a yellow solid. mp. 173–174° C.; $^1$H-NMR (CDCl$_3$)δ 12.96 (s, 1H), 8.68 (s, 1H), 8.43 (d, J=2.7 Hz, 1H), 8.36 (dd, J=9.3, 2.7 Hz, 1H), 7.70 (s, 2H), 7.17 (d, J=9.3 Hz, 1H); $^{13}$C-NMR (CDCl$_3$) δ 168.7, 166.1, 145.7, 140.1, 129.4, 129.1, 127.6, 125.8, 125.7, 118.5, 116.9; HRMS (CI) calcd for $C_{14}H_{11}N_2O_3F_3Cl_2$ [M+H]$^+$ 378.9864, found 378.9866.

Schiff Base 6f ($R^1$=6-Me-4-NO$_2$, $R^2$=2,6-i-Pr$C_6H_3$):

3-Methyl-5-nitrosalicylaldehyde (0.63 g, 3.40 mmol), 2,6-diisopropylaniline (0.80 g, 3.40 mmol) and ethanol (20 mL) afforded 1.10 g (95%) of the title compound as a yellow solid. mp. 120–121° C.; $^1$H-NMR (CDCCl$_3$) δ 14.50 (s, 1H), 8.38 (s, 1H), 8.21 (s, 1H), 7.23 (s, 4H), 2.95 (septet, J=6.9 Hz, 2H), 2.42 (s, 3H), 1.20 (d, J=6.9 Hz, 12H); $^{13}$C-NMR (CDCl$_3$) δ 165.4, 144.4, 139.1, 138.5, 132.9, 128.5, 128.2, 126.0,125.9, 123.2, 116.3, 28.0, 23.3, 15.4; HRMS (DCI) $C_{20}H_{25}N_2O_3$ [M+H]$^+$ 341.1865, found 341.1873.

Schiff Base 6g ($R^1$=4-NO$_2$, $R^2$=2,6-i-Pr-4-NO$_2$-$C_6H_2$):

5-Nitrosalicylaldehyde (1.0 g, 6.0 mmol), 2,6-diisopropyl-4-nitroaniline (1.30 g, 6.0 mmol) and ethanol (20 mL) afforded 2.0 g (91%) of the title compound as a yellow solid. mp. 118–120° C.; $^1$H-NMR (CDCl$_3$) δ 13.34 (s, 1H), 8.43 (s, 2H), 8.33 (dd, J=9.0, 2.4 Hz, 1H), 8.09 (s, 2H), 7.18 (d, J=9.0 Hz, 1H), 3.00 (septet, J=6.9 Hz, 2H), 1.23 (d, J=6.9 Hz, 12H); $^{13}$C-NMR (CDCl$_3$) δ 166.0, 165.7, 150.3, 145.8, 140.3, 134.0, 128.8, 128.6, 118.9, 118.1, 117.1, 28.3, 22.6;

HRMS (DCI) $C_{19}H_{22}N_3O_5$ [M+H]$^+$372.1559, found 372.1560.

Schiff Base 6h ($R^1$=4-NO$_2$, $R^2$=1-adamantanemethyl):

5-Nitrosalicylaldehyde (0.84 g, 5.0 mmol), 1-adamantanemethylaniline (0.90 g, 5.0 mmol) and ethanol (15 mL) afforded 1.40 g (92%) of the title compound as a yellow solid. mp. 178–180° C.; $^1$H-NMR (CDCl$_3$) δ 15.18 (s, 1H), 8.21 (s, 1H), 8.16 (t, J=9.0 Hz, 2H), 6.86 (d, J=9.3 Hz, 1H), 3.29 (s, 2H), 2.00 (s, 3H), 1.65 (m, 6H), 1.55 (bs, 6H); $^{13}$C-NMR (CDCl$_3$) 172.9, 164.4, 137.2, 129.1, 128.5, 120.4, 115.1, 68.4, 40.1, 33.9, 27.9; HRMS (DCI) $C_{18}H_{23}N_2O_3$ [M+ H]$^+$315.1709, found 315.1710.

General Procedure for the Preparation of Thallium Salts (7a–h).

To a solution of the appropriate Schiff base (6a–h) in benzene or THF (10 mL), a solution of thallium ethoxide in benzene or THF (5 mL) was added dropwise at room temperature. Using a glass pipette, the solution of thallium ethoxide in benzene or THF was filtered through a plug of glasswool to remove any impurities. Immediately after the addition, a pale yellow solid formed and the reaction mixture was stirred for 2 hour at room temperature. Filtration of the solid under a nitrogen or argon atmosphere gave the respective thallium salt (7a–h) in quantitative yield. The salt was immediately used in the next step without further purification.

General Procedure for the Preparation of Schiff Base Substituted Ruthenium Complexes (8a–h).

A solution of the appropriate thallium salt (7a–h) in THF (5 mL) was added to a solution of ruthenium complex 3 in THF (5 mL). The reaction mixture was 5 stirred at room temperature for 3 hours. After evaporation of the solvent, the residue was dissolved in a minimal amount of benzene and cooled to 0° C. The thallium chloride (the byproduct of the reaction) was removed via filtration. The desired complex was then washed with cold benzene (10 mL×3) and the filtrate was evaporated. The solid residue was recrystallized from pentane (–70° C.) to give the respective Schiff base substituted ruthenium complex (8a–h) in moderate to good yield as a brown solid. Any modifications are described below for each reaction.

Ruthenium Schiff Base Complex 8a:

Ruthenium complex 3 (1.20 g, 1.50 mmol), thallium salt 7a (0.78 g, 1.60 mmol), and THF (20 mL) afforded 0.89 g (75%) of the title complex as a brown solid. mp. 119–122° C.; $^1$H-NMR (CD$_2$Cl$_2$) δ 19.68 (d, J=3.6 Hz, 1H), 8.06 (d, J=5.4 Hz, 1H), 7.92 (d, J=7.5 Hz, 2H), 7.53 (t, J=7.2 Hz, 1H), 7.33–7.00 (m, 8H), 6.60 (t, J=7.2 Hz, 1H), 3.36 (septet, J=6.9 Hz, 1H), 2.51 (q, J=11.7 Hz, 3H), 2.13 (septet, J=6.9 Hz, 1H), 1.79–1.52 (m, 20H), 1.38 (d, J=6.6 Hz, 3H), 1.22 (m, 10H), 1.11 (d, J=6.9 Hz, 3H), 0.75 (dd, J=21.3, 6.9 Hz, 6H); $^{31}$P-NMR (CD$_2$Cl$_2$) δ 6 52.23; MS (FAB) 787 (3), 386 (12), 315 (26), 297 (19), 281 (49), 279 (19), 255 (8), 231 (20), 154 (23), 119 (23), Ruthenium Schiff Base Complex 8b:

Ruthenium complex 3 (1.65 g, 2.0 mmol), thallium salt 7b (1.10 g, 2.10 mmol), and THF (40 mL) afforded 1.40 g (82%) of the title complex as a brown solid. mp. 140–145° C.; $^1$H-NMR (CD$_2$Cl$_2$) δ 19.77 (d, J=3.3 Hz, 1H), 8.27 (d, J=2.7 Hz, 1H), 8.14 (d, J=5.4 Hz, 1H), 8.10 (dd, J=9.6, 2.7 Hz, 1H), 7.94 (d, J=7.8 Hz, 2H), 7.60 (t, J=7.2 Hz, 1H), 7.30 (t, J=7.8 Hz, 2H), 7.21 (m, 2H) 7.09 (dd, J=6.9, 1.8 Hz, 1H), 6.99 (d, J=9.3 Hz, 1H), 3.26 (septet, J=6.6 Hz, 1H), 2.52 (q, J=11.5 Hz, 3H), 2.11 (septet, J=6.6 Hz, 1H), 1.73 (bs, 20H), 1.40 (d, J=6.6 Hz, 3H), 1.23 (m, 10H), 1.15 (d, J=6.9 Hz, 3H), 0.78 (dd, J=17.4, 6.9 Hz, 6H); $^{31}$P-NMR (CD$_2$Cl$_2$) δ 52.23; HRMS (FAB) C$_{44}$H$_{60}$ClN$_2$O$_3$PRu [M]$^+$832.3074, found 832.3104.

Ruthenium Schiff Base Complex 8c:

Ruthenium complex 3 (0.25 g, 0.30 mmol), thallium salt 7c (0.16 g, 0.32 mmol), and THF (3 mL) afforded 0.13 g (54%) of the title complex as a brown solid. mp. 139–142° C.; $^1$H-NMR (CD$_2$Cl$_2$) δ 19.49 (d, J=4.7 Hz, 1H), 8.22 (d, J=2.8 Hz, 1H), 8.08 8.04 (m, 3H), 7.98 (d, J=7.8 Hz, 2H), 7.56 (d, J=7.4 Hz, 1H), 7.35 (d, J=1.3 Hz, 1H), 7.27 (t, J=7.5 Hz, 2H), 7.00 (d, J=9.6 Hz, 1H), 3.79 (s, 3H), 2.38 (s, 6H), 1.75–1.21 (m, 30H); $^{31}$P-NMR (CD$_2$Cl$_2$) δ 6 50.51; HRMS (FAB) C$_{41}$H$_{54}$ClN$_2$O$_4$PRu [M]$^+$806.2553, found 806.2520.

Ruthenium Schiff Base Complex 8d:

Ruthenium complex 3 (0.41 g, 0.50 mmol), thallium salt 7d (0.32 g, 0.55 mmol), and THF (25 mL) afforded 0.35 g (80%) of the title complex as a brown solid. mp. 128–131° C.; $^1$H-NMR (CD$_2$Cl$_2$) δ 19.48 (d, J=4.8 Hz, 1H), 8.22 (d, J=2.7 Hz, 1H), 8.07 (dd, J=9.3, 2.7 Hz, 1H), 8.03 (d, J=5.7 Hz, 1H), 7.98 (d, J=7.8 Hz, 2H), 7.58 (t, J=7.8 Hz, 1H), 7.28 (t, J=7.8 Hz, 2H), 7.17 (s, 1H), 7.00 (d, J=9.6 Hz, 1H), 2.47 (q, J=12.0 Hz, 3H), 2.37 (s, 3H), 1.78–1.63 (bs, 20H), 1.50 (d, J=13.5 Hz, 3H), 1.30–1.16 (m, 10H); $^{31}$P-NMR (CD$_2$Cl$_2$) δ 50.62; HRMS (FAB) C$_{40}$H$_{51}$BrClN$_2$O$_3$PRu [M]$^+$856.1532, found 856.1573.

Ruthenium Schiff Base Complex 8e:

Ruthenium complex 3 (0.34 g, 0.40 mmol), thallium salt 7e (0.26 g, 0.44 mmol), and THF (20 mL) afforded 0.30 g (85%) of the title complex as a brown solid. mp. 145–149° C.; $^1$H-NMR (CD$_2$Cl$_2$) δ 19.39 (d, J=4.5 Hz, 1H), 8.25 (d, J=2.7 Hz, 1H), 8.09 (dd, J=9.3, 2.7 Hz, 1H), 7.99 (m, 3H), 7.69 (d, J=18.0 Hz, 1H), 7.57 (t, J=7.2 Hz, 1H), 7.35 (s, 1H), 7.28 (t, J=7.8 Hz, 1H), 7.02 (d, j=9.6 Hz, 1H), 2.48 (q, J=11.7 Hz, 3H), 1.73–1.54 (m, 15H), 1.39 (m, 5H), 1.22 (bs, 10H); $^{31}$P-NMR (CD$_2$Cl$_2$) δ 50.65; HRMS (FAB) C$_{39}$H$_{45}$Cl$_3$F$_3$N$_2$O$_3$PRu [M]$^+$ 886.1199, found 886.1179.

Ruthenium Schiff Base Complex 8f:

Ruthenium complex 3 (0.82 g, 1.0 mmol), thallium salt 7f (0.60 g, 1.10 mmol), and THF (35 mL) afforded 0.68 g (80%) of the title complex as a brown solid. mp. 155–158° C.; $^1$H-NMR (CD$_2$Cl$_2$) δ 19.69 (d, J=2.7 Hz, 1H), 8.11 (d, J=4.5 Hz, 2H), 7.89 (d, J=7.8 Hz, 1H), 7.55 (t, J=7.2 Hz, 1H), 7.33 (s, 1H), 7.24 (t, J=7.5 Hz, 2H), 7.17 (m, 3H), 7.07 (d, J=7.2 Hz, 1H), 3.22 (septet, J=6.6 Hz, 1H), 2.58 (q, J=11.4 Hz, 3H), 2.38 (s, 3H), 1.91 (septet, J=6.6 Hz, 1H), 1.80–1.54 (m, 20H), 1.36 (d, J=6.6 Hz, 3H), 1.19 (bs, 13H), 1.10 (d, J=6.6 Hz, 3H), 0.85 (d, J=6.9 Hz, 3H), 0.72 (d, J=6.3 Hz, 3H); $^{31}$P-NMR (CD$_2$Cl$_2$) δ 53.50; HRMS (FAB) C$_{45}$H$_{62}$ClN$_2$O$_3$PRu [M]$^+$846.3230, found 846.3279.

Ruthenium Schiff Base Complex 8g:

Ruthenium complex 3 (0.66 g, 0.80 mmol), thallium salt 7g (0.51 g, 0.88 mmol), and THF (50 mL) afforded 0.59 g (67%) of the title complex as a brown solid. mp. 160–163° C.; $^1$H-NMR (CD$_2$Cl$_2$) δ 19.72 (d, J=3.3 Hz, 1H), 8.30 (d, J=2.7 Hz, 1H), 8.13 (d, J=3.0 Hz, 1H), 8.10 (s, 2H), 8.05 (d, J=2.1 Hz, 1H), 7.95 (d, J=2.4 Hz, 1H), 7.92 (d, J=7.8 Hz, 2H), 7.61 (t, J=7.2 Hz, 1H), 7.30 (t, J=7.8 Hz, 2H), 7.00 (d, J=9.6 Hz, 1H), 3.29 (septet, J=6.6 Hz, 1H), 2.48 (q, J=11.4 Hz, 2H), 2.18 (septet, J=6.6 Hz, 1H), 1.72 (bs, 20H), 1.45 (d, J=6.9 Hz, 3H), 1.20 (m, 13H), 0.80 (dd, J=21.0, 6.6 Hz, 6H); $^{31}$P-NMR (CD$_2$Cl$_2$) δ 52.54; HRMS (FAB) C$_{44}$H$_{59}$ClN$_3$O$_5$PRu [M]$^+$877.2924, found 877.2887.

Ruthenium Schiff Base Complex 8h:

Ruthenium complex 3 (0.33 g, 0.40 mmol), thallium salt 7h (0.23 g, 0.44 mmol), and THF (20 mL) afforded 0.18 g (54%) of the title complex as a brown solid. mp. 162–166° C.; $^1$H-NMR (CD$_2$Cl$_2$) δ 18.68 (d, J=13.5 Hz, 1H), 7.95 (dd, J=9.3 Hz, 1H), 7.89 (d, J=7.5 Hz, 2H), 7.79 (d, J=3.0 Hz, 1H), 7.64(t, j=7.5 Hz, 1H), 7.38 (d, J=7.5 Hz, 1H), 7.30 (t, J=7.8 Hz, 1H), 6.97 (d, J=9.3 Hz, 1H), 6.09 (d, J=10.8 Hz, 1H), 3.00 (dd, J=10.8, 2.7 Hz, 2H), 2.29 (q, J=11.4 Hz, 3H), 1.99 (bs, 3H), 1.84 (bs, 3H), 1.73 (m, 20H), 1.57 (m, 10H), 1.25 (d, J=8.7 Hz, 9H); $^{31}$P-NMR (CD$_2$Cl$_2$) 38.95; HRMS (FAB) C$_{43}$H$_{60}$ClN$_2$O$_3$PRu [M]$^+$820.3074, found 820.3079.

General Procedure for the Ring-Closing Metathesis of Diethyl Diallylmalonate using Ruthenium Schiff Base Catalysts 8a–h.

All reactions were performed on the benchtop in air by weighing 8 mol % of the respective catalyst (8a–h) into a dry NMR tube and dissolving the solid in 0.5 ml of CD$_2$Cl$_2$ or C$_6$D$_6$. A solution of diethyl diallylmalonate (0.1 mmol) in CD$_2$Cl$_2$ or C$_6$D$_6$ (0.5 mL) was added. The tube was then capped, wrapped with parafilm, and shaken periodically. The studies were ran at both ambient temperatures and higher temperatures (~65° C.) to access the activity and stability of the catalysts during the course of the reactions. Product formation and diene disappearance were monitored by integrating the allylic methylene peaks.

X-ray Structure of the Ruthenium Complex 8b.

Crystals suitable for X-ray structure determination were grown from a solution of isopropyl ether at −20° C. over a few days. The brown crystal used for data collection was 0.10 mm×0.13 mm×0.44 mm. Data collection was carried out at 160 K. A total of 17106 reflections were collected, 7741 of which were independent. Data collection parameters are summarized in part by the Table 2. The structure was solved by direct methods using the Siemens SHELXS-86 program. The molecule was refined isotropically (with riding H atoms on dichloromethane solvent) with a fractional population parameter for each solvent molecule also refined. The hydrogen atoms were originally placed at calculated positions. Eventually, the coordinates of all but two (H38a and H38b) were refined, with Uiso's fixed at 1.2 times the Ueq of the attached atom. Refinement was full-matrix least-squares using SHELXL-93.

Decomposition Experiment with Ruthenium Complexes 3 and 8b.

Two NMR tube samples were prepared in toluene-d8, one containing 4.0 mmolar of 8b and the other containing 4.2 mmolar of 3, with an internal standard of anthracene. The samples were analyzed by $^1$H-NMR and placed in an 85° C. oil bath. After 30 minutes, the samples were again analyzed and replaced into the oil bath. After another 30 minutes, a final analysis by NMR was performed. For eacy analysis, the intensity of the carbene signal in the NMR was determined relative to the anthracene signal and used to calculate the molar concentration of the respective remaining carbene catalyst.

What is claimed is:

1. A compound of the general formula of the formula

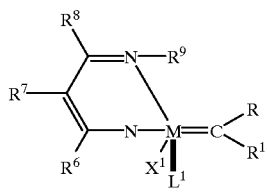

wherein:

M is ruthenium or osmium;

$X^1$ an anionic ligand;

$L^1$ is a neutral electron donor;

R and $R^1$ are each hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, the substituent optionally substituted with one or more moieties selected from the group consisting $C_1$–$C_{10}$ alkyl, $C_1$–$C_{10}$ alkoxy, and aryl;

Z is selected from the group consisting of oxygen, sulfur, —$NR^{10}$, and —$PR^{10}$, and $R^6$, $R^7$, $R^8$, $R^9$, and $R^{10}$ are each selected from the group consisting of hydrogen, $C_1$–$C_{20}$ alkyl, aryl, and heteroaryl, each non-hydrogen group optionally substituted with one or more moieties selected from the group consisting of $C_1$–$C_{10}$ alkyl, $C_1$–$C_{10}$ alkoxy, and aryl;

wherein $X^1$, $L^1$, Z, R, $R^1$, $R^6$, $R^7$, $R^8$, and $R^9$ each optionally includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

2. The compound of claim 1 wherein

M is ruthenium;

R is hydrogen;

$R^1$ is selected from the group consisting of $C_1$–$C_{20}$ alkyl, $C_2$–$C_{20}$ alkenyl, and aryl;

$L^1$ is a phosphine of the formula $PR^3R^4R^5$ wherein $R^3$, $R^4$, and $R^5$ are each selected from the group consisting of aryl, $C_1$–$C_{10}$ primary alkyl, secondary alkyl, and cycloalkyl; and, $X^1$ is selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and, trifluoromethanesulfonate.

3. The compound as in claim 2 wherein:

$X^1$ is chloride;

$L^1$ is selected from the group consisting of -P(cyclohexyl)$_3$, -P(cyclopentyl)$_3$, -P(isopropyl)$_3$, and -P(phenyl)$_3$;

$R^1$ is phenyl or vinyl, optionally substituted with one or more moeties selected from the group consisting of $C_5$–$C_5$ alkyl, $C_5$–$C_5$ alkoxy, and phenyl;

$R^6$ and $R^7$ together form an aryl or heteroaryl group;

$R^8$ is hydrogen; and, $R^9$ is aryl or heteroaryl.

4. The compound as in claim 3 wherein $R^6$ and $R^7$ together forms a phenyl group; and, $R^9$ is phenyl.

5. A compound of the formula

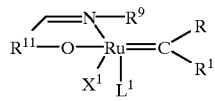

wherein:

$X^1$ is an anionic ligand;

$L^1$ is a neutral electron donor;

R and $R^1$ are each hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfinyl, the substituent optionally substituted with one or more moieties selected from the group consisting $C_1$–$C_{10}$ alkyl, $C_1$–$C_{10}$ alkoxy, and aryl;

$R^9$ is selected from the group consisting of hydrogen, $C_1$–$C_{20}$ alkyl, aryl, and heteroaryl, the non-hydrogen groups optionally substituted with one or more moieties selected from the group consisting of $C_1$–$C_{10}$ alkyl, $C_1$–$C_{10}$ alkoxy, and aryl; and, $R^{11}$ is an aryl or heteroaryl, optionally substituted with one or more moieties selected from the group consisting of $C_1$–$C_{10}$ alkyl, $C_1$–$C_{10}$ alkoxy, and aryl;

wherein $X^1$, $L^1$, R, $R^1$, $R^9$, and $R^{11}$ each optionally includes one or more functional groups selected from the group consisting hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

6. The compound as in claim 5 wherein $X^1$ is selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and, trifluoromethanesulfonate;

$L^1$ is a phosphine of the formula $PR^3R^4R^5$ where $R^3$, $R^4$, and $R^5$ are each selected from the group consisting of aryl, $C_1$–$C_{10}$ primary alkyl, secondary alkyl, and cycloalkyl;

R is hydrogen; and, $R^1$ is selected from the group consisting of $C_1$–$C_{20}$ alkyl, $C_2$–$C_{20}$ alkenyl, and aryl.

7. The compound as in claim 6 wherein $X^1$ is chloride;

$L^1$ is selected from the group consisting of -P(cyclohexyl)$_3$, -P(cyclopentyl)$_3$, -P(isopropyl)$_3$; and -P(phenyl)$_3$;

$R^1$ is phenyl or vinyl, optionally substituted with one or more moieties selected from the group consisting of $C_1$–$C_5$ alkyl, $C_1$–C5 alkoxy, and phenyl; and, $R^9$ and $R^{11}$ are each aryl or heteroaryl.

8. The compound as in claim 7 wherein $R^9$ and $R^{11}$ are each phenyl.

9. The compound as in claim 7 wherein $R^9$ and $R^{11}$ are both phenyl substituted with one or more moieties selected from the group consisting of $C_1$–$C_{10}$ alkyl, $C_1$–$C_{10}$ alkoxy, and aryl, the $R^9$ and $R^{11}$ groups each optionally including one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

10. The compound as in claim 9 having the formula

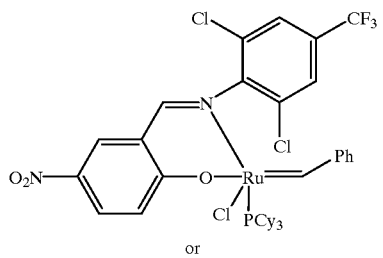

or

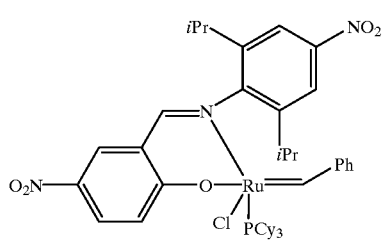

11. A method for preparing a catalyst having the formula

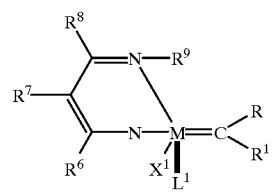

comprising contacting a salt of a Schiff base having the formula

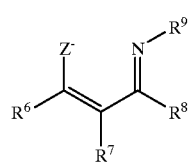

with compound having the formula

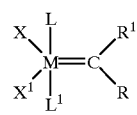

wherein:
M is ruthenium or osmium;
X and $X^1$ are each an anionic ligand;
L and $L^1$ are each a neutral electron donor;
R and $R^1$ are each hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, the substituent optionally substituted with one or more moieties selected from the group consisting $C_1$–$C_{10}$ alkyl, $C_1$–$C_{10}$ alkoxy, and aryl;

Z is selected from the group consisting of oxygen, sulfur, —$NR^{10}$, and —$PR^{10}$, and
$R^6$, $R^7$, $R^8$, $R^9$, and $R^{10}$ are each selected from the group consisting of hydrogen, $C_1$–$C_{20}$ alkyl, aryl, and heteroaryl, each non-hydrogen group optionally substituted with one or more moieties selected from the group consisting of $C_1$–$C_{10}$ alkyl, $C_1$–$C_{10}$ alkoxy, and aryl;
wherein $X^1$, $L^1$, Z, R, $R^1$, $R^6$, $R^7$, $R^8$, and $R^9$ each optionally includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

12. The method as in claim 11 wherein the salt of the Schiff base is a thallium salt.

13. The method as in claim 12 wherein
M is ruthenium;
R is hydrogen;
$R^1$ is selected from the group consisting of $C_1$–$C_{20}$ alkyl, $C_2$–$C_{20}$ alkenyl, and aryl;
L and $L^1$ are each a phosphine of the formula $PR^3R^4R^5$ where $R^3$, $R^4$, and $R^5$ are each selected from the group consisting of aryl, $C_1$–$C_{10}$ primary alkyl, secondary alkyl, and cycloalkyl; and,
X and $X^1$ are each selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and, trifluoromethanesulfonate.

14. The compound as in claim 13 wherein:
X and $X^1$ are each chloride;
L and $L^1$ are each selected from the group consisting of -P(cyclohexyl)$_3$, -P(cyclopentyl)$_3$, -P(isopropyl)$_3$; and -P(phenyl)$_3$;
$R^1$ is phenyl or vinyl, optionally substituted with one or more moieties selected from the group consisting of $C_1$–$C_5$ alkyl, $C_1$–$C_5$ alkoxy, and phenyl;
$R^6$ and $R^7$ together form an aryl or heteroaryl group;
$R^8$ is hydrogen; and,
$R^9$ is aryl or heteroaryl.

15. The compound as in claim 14 wherein
$R^6$ and $R^7$ together forms a phenyl group; and,
$R^9$ is phenyl.

16. A method of preparing a catalyst having the formula

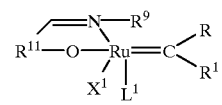

comprising contacting a salt a Schiff base having the formula $R^{11}(HC=NR^9)(O^-)$ with a compound having the formula

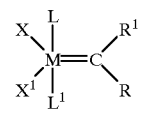

wherein:
$X^1$ are each an anionic ligand;
L and $L^1$ are each a neutral electron donor;
R and $R^1$ are each hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, the substituent optionally substituted with one or more moieties selected from the group consisting $C_1$–$C_{10}$ alkyl, $C_1$–$C_{10}$ alkoxy, and aryl;

$R^9$ is selected from the group consisting of hydrogen, $C_1$–$C_{20}$ alkyl, aryl, and heteroaryl, the non-hydrogen groups optionally substituted with one or more moieties selected from the group consisting of $C_1$–$C_{10}$ alkyl, $C_1$–$C_{10}$ alkoxy, and aryl; and, $R^{11}$ is an aryl or heteroaryl, optionally substituted with one or more moieties selected from the group consisting of $C_1$–$C_{10}$ alkyl, $C_1$–$C_{10}$ alkoxy, and aryl, wherein $X^1$, $L^1$, R, $R^1$, $R^9$, and $R^{11}$ each optionally includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

17. The method as in claim 16 wherein the salt of the Schiff base is a thallium salt.

18. The method as in claim 16 wherein

X and $X^1$ are each selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and, trifluoromethanesulfonate;

L and $L^1$ are each a phosphine of the formula $PR^3R^4R^5$ where $R^3$, $R^4$, and $R^5$ are each aryl, $C_1$–$C_{10}$ primary alkyl, secondary alkyl, or cycloalkyl;

R is hydrogen; and, $R^1$ is selected from the group consisting of $C_1$–$C_{20}$ alkyl, $C_2$–$C_{20}$ alkenyl, and aryl.

19. The method as in claim 18 wherein

X and $X^1$ are each chloride;

L and $L^1$ are each -P(cyclohexyl)$_3$, -P(cyclopentyl)$_3$, -P(isopropyl)$_3$, and -P(phenyl)$_3$;

$R^1$ is phenyl or vinyl, optionally substituted with one or more moieties selected from the group consisting of $C_1$–$C_5$ alkyl, $C_1$–$C_5$ alkoxy, and phenyl; and $R^9$ and $R^{11}$ are each aryl or heteroaryl.

20. The method as in claim 19 wherein $R^9$ and $R^{11}$ are each phenyl.

21. The method as in claim 19 wherein $R^9$ and $R^{11}$ are both phenyl substituted with one or more moieties selected from the group consisting of $C_1$–$C_{10}$ alkyl, $C_1$–$C_{10}$ alkoxy, and aryl; the $R^9$ and $R^{11}$ groups each optionally including one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

22. The method as in claim 21 wherein the catalyst has the formula

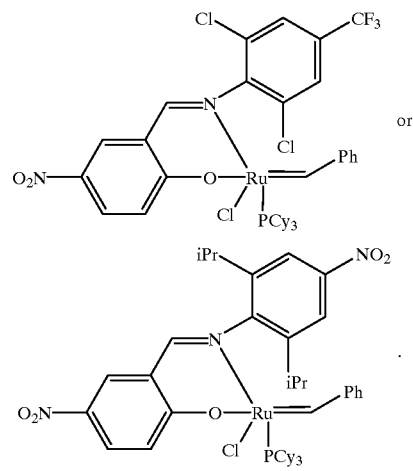

23. A method for performing a metathesis reaction comprising contacting an olefin with a catalyst having the formula

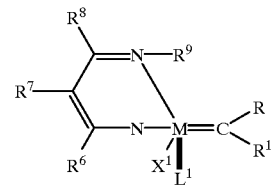

wherein:

M is ruthenium or osmium;

$X^1$ is an anionic ligand;

$L^1$ is a neutral electron donor;

R and $R^1$ are each hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, the substituent optionally substituted with one or more moieties selected from the group consisting $C_1$–$C_{10}$ alkyl, $C_1$–$C_{10}$ alkoxy, and aryl;

Z is selected from the group consisting of oxygen, sulfur, —$NR^{10}$, and —$PR^{10}$, and $R^6$, $R^7$, $R^8$, $R^9$, and $R^{10}$ are each selected from the group consisting of hydrogen, $C_1$–$C_{20}$ alkyl, aryl, and heteroaryl, each non-hydrogen group optionally substituted with one or more moieties selected from the group consisting of $C_1$–$C_{10}$ alkyl, $C_1$–$C_{10}$ alkoxy, and aryl;

wherein $X^1$, $L^1$, Z, R, $R^1$, $R^6$, $R^7$, $R^8$, and $R^9$ each optionally includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

24. The method as in claim 23 wherein the olefin is a cyclic olefin.

25. A method for molding articles comprising (i) adding to a mold at room temperature an olefin and a catalyst having the formula

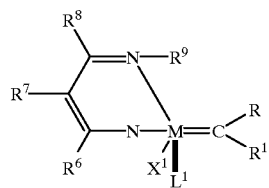

wherein:

M is ruthenium or osmium;

$X^1$ is an anionic ligand;

$L^1$ is a neutral electron donor;

R and $R^1$ are each hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, the substituent optionally substituted with one or more moieties selected from the group consisting $C_1$–$C_{10}$ alkyl, $C_1$–$C_{10}$ alkoxy, and aryl;

Z is selected from the group consisting of oxygen, sulfur, —$NR^{10}$, and —$PR^{10}$, and $R^6$, $R^7$, $R^8$, $R^9$, and $R^{10}$ are each selected from the group consisting of hydrogen, $C_1$–$C_{20}$ alkyl, aryl, and heteroaryl, each non-hydrogen group optionally substituted with one or more moieties selected from the group consisting of $C_1$–$C_{10}$ alkyl, $C_1$–$C_{10}$ alkoxy, and aryl;

wherein $X^1$, $L^1$, Z, R, $R^1$, $R^6$, $R^7$, $R^8$, and $R^9$ each optionally includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen and (ii) bringing the mold to a temperature of at least 40° C.

\* \* \* \* \*